United States Patent
Lynch et al.

[11] Patent Number: 5,366,467
[45] Date of Patent: Nov. 22, 1994

[54] ENDOSCOPIC SCISSORS

[75] Inventors: Robert S. Lynch, Durham, N.C.; Peter Wester, Millburn, N.J.

[73] Assignee: Linvatec Corporation, Largo, Fla.

[21] Appl. No.: 914,253

[22] Filed: Jul. 15, 1992

[51] Int. Cl.$^5$ ............................................. A61B 17/32
[52] U.S. Cl. .................................................. 606/174
[58] Field of Search .................... 606/45, 52, 79, 151, 606/170, 171, 174, 167

[56]  References Cited
U.S. PATENT DOCUMENTS

| | | |
|---|---|---|
| 2,668,537 | 2/1954 | Kapp . |
| 3,454,009 | 11/1966 | Hunnicutt ............................ 606/208 |
| 3,823,719 | 7/1974 | Cummings ........................... 606/151 |
| 3,877,145 | 4/1975 | Andrews .............................. 606/174 |
| 3,894,336 | 7/1975 | Desimone ............................ 606/174 |
| 3,895,636 | 7/1975 | Schmidt . | 
| 4,823,792 | 4/1989 | Dulebohn et al. ................... 606/151 |
| 4,944,093 | 7/1990 | Falk . |
| 5,147,357 | 9/1992 | Rose et al. ............................. 606/49 |
| 5,156,633 | 10/1992 | Smith ................................... 606/170 |

*Primary Examiner*—C. Fred Rosenbaum
*Attorney, Agent, or Firm*—Gene Warzecha

[57]  ABSTRACT

A pair of endoscopic scissors having an actuating means at the proximal end and a pair of pivotable scissor blades at the distal end. The actuating means is adapted to be squeezed to a predetermined point when the scissor blades are fully closed, at least one of the blades being provided with a stop surface adjacent its proximal end in order to prevent the blade tips from crossing over each other in their fully closed position. The gap between the actuating means at the proximal end of the instrument enable the application of additional force between the pivotable scissor blades without causing the blades to cross-over each other.

2 Claims, 4 Drawing Sheets

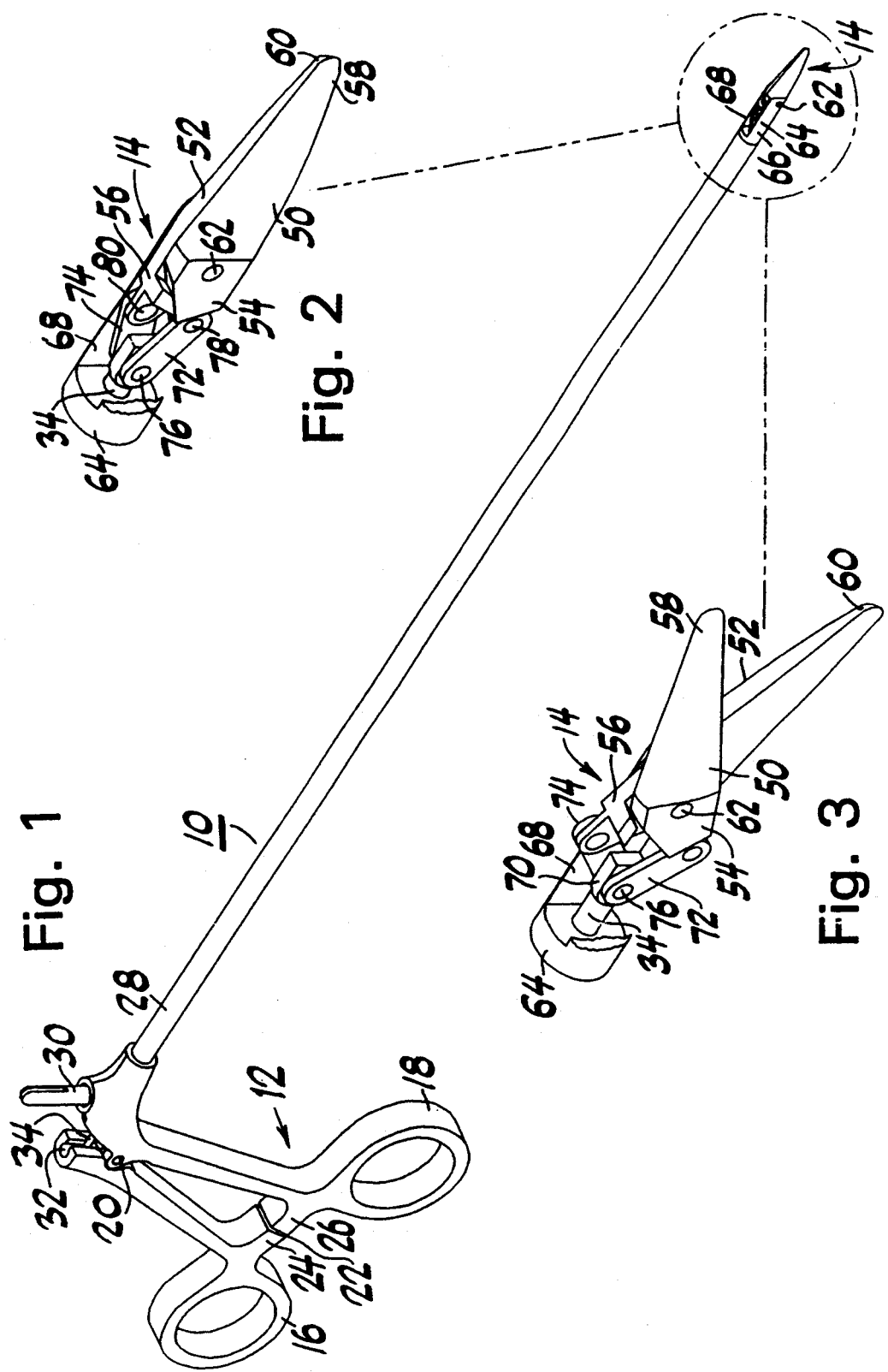

ENDOSCOPIC SCISSORS

BACKGROUND OF THE INVENTION

1. Field of the Invention

The invention relates generally to surgical instruments. In particular, the invention relates to endoscopic instruments and, more particularly, to means for increasing the forces which are able to be exerted by a pair of scissor blades operating at the distal tip of an endoscopic instrument.

2. Description of the Prior Art

Scissors are an obviously well-known type of surgical instrument. With the recent interest in endoscopic surgery in which surgical procedures are performed through one or more cannulas inserted into the body, there has been a commensurate interest in developing endoscopic instruments—scissors and others—which are operable through relatively narrow diameter cannulas.

The general approach to developing such endoscopic instruments has been to adapt known, open-surgical-procedure instruments to endoscopic use by separating the handle portion of such instrument from the working elements by means of interposing an extended shaft. One well-accepted design of endoscopic instruments incorporates a pair of ring handles pivotably joined to each other and to the proximal end of an elongated support shaft which is secured to one of the ring handles. The other ring handle is operatively connected to an actuating rod which is aligned along the axis of the support shaft. Pivoting the ring handles about their pivot point produces a longitudinal motion of the actuating rod relative to the support shaft. By connecting various working elements to the distal ends of the support shaft and the actuating rod, the pivoting motion of the ring handles may be translated into pivoting motion of the working elements relative to each other at the distal tip of the endoscopic instrument. In the case of scissors, the working elements are a pair of scissor blades.

While this relatively straightforward way of adapting open-surgical-procedure instruments to endoscopic use is of some value for many types of instruments, there are some limitations which limit the acceptability of this approach for certain instruments. For example, the forces which are able to be transmitted from the ring handles of a pair of endoscopic scissors to the distal tip of the instrument via elongated actuating rods are constrained by certain design parameters. In conventional non-endoscopic scissors the forces applied to the blades by the ring handles (before they touch) are almost directly representative of the force on the handles because each handle has a blade associated with it, both being on opposite sides of a single shaft. In endoscopic scissors, however, the various linkages and elongated components tend to be elastic enough to stretch slightly such that squeezing of the ring handles to their fully closed position does not necessarily result in complete cutting because the distal tips of the scissor blades may be held open by tough tissue. In the case of conventional endoscopic scissors the ring handles are adjusted so that when they are squeezed together they contact each other when the scissor blades are fully aligned (i.e. closed) without crossing over each other. This adjustment is made without any tissue interposed between the blades. No greater force may be applied when the ring handles touch and, therefore, if tough tissue is interposed the scissor blades merely stay open causing an incomplete cut. There is a need for some means to apply greater cutting force to endoscopic scissors.

Merely adjusting the ring handles so the blades are aligned when the handles are separated and permitted to be squeezed more, is an obvious but insufficient solution. If this were done, further squeezing of the handles could cause further pivoting of the scissor blades such that their distal tips would pass each other. The crossing over of the distal tips of scissor blades is particularly undesirable in endoscopic applications since the crossed over blades will result in sharp and dangerous tips which may be inadvertently harmful to adjacent tissue at the endoscopic work site.

It is accordingly an object of this invention to produce a surgical instrument in which the application of force from the proximal end of the instrument to its distal tip is optimized.

It is a further object of this invention to provide a surgical instrument in which an actuating means at the proximal end of the instrument is able to apply force between a pair of working elements at the distal tip of the instrument even after the working elements have reached their fully closed position.

It is a further object of this invention to provide scissors for use in endoscopic surgical procedures wherein the scissors are provided with means to prevent their tips from crossing over.

It is another object of this invention to produce a pair of endoscopic scissors which is easier to adjust in manufacturing.

SUMMARY OF THE INVENTION

These and other objects of the invention are achieved by the preferred embodiment of the invention disclosed herein which is a pair of scissors adapted for use in endoscopic surgical procedures. The scissors are provided with an actuating means at their proximal end and a pair of scissor blades movable relative to each other at the distal end of the instrument. An interconnecting means is provided to operatively join the actuating means and the scissor blades and a stop means is provided at the distal end of the scissors for preventing the scissor blades from crossing over each other. In one embodiment, the stop means is a stop surface extending transversely from one of the scissor blades into the path of the other. The stop surface prevents the two scissor blades from moving past each other even if the actuating means at the proximal end of the instrument is attempting to apply a greater than normal amount of force.

BRIEF DESCRIPTION OF THE DRAWINGS

FIG. 1 is a front perspective view of an endoscopic scissors constructed in accordance with the principles of this invention.

FIG. 2 is an exploded view of the distal tip of the instrument of FIG. 1 showing the scissor blades in a closed position.

FIG. 3 is an exploded view of the distal tip of the instrument of FIG. 1 showing the scissor blades in an open position.

DESCRIPTION OF THE PREFERRED EMBODIMENT

Figure 4A:
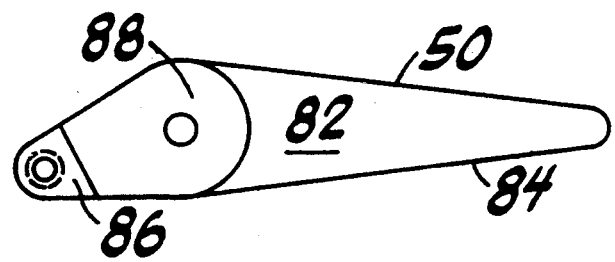
FIGS. 4a, b and c are top plan, side elevation and bottom plan views, respectively, of one of the scissor blades of the instrument of FIG. 1.

Referring now to FIG. 1, there is shown a pair of scissors 10 for use in surgical procedures and particularly suited for endoscopic surgical procedures. These scissors will occasionally be referred to herein as "endoscopic scissors" and it will be understood that these scissors are usable in all surgical procedures in which instruments are inserted through a tube or cannula or passageway. As such, the term "endoscopic" encompasses arthroscopy, laparoscopy, etc. Depending upon the length of the instrument, it will be adaptable to a variety of endoscopic procedures and will also be suitable for open surgical procedures.

Endoscopic scissors 10 comprise an actuating means 12 at the proximal end of the instrument and a working element 14 at the distal end of the instrument. Actuating member 12 includes a pair of ring handles 16 and 18 pivotably connected at 20 in a well-known manner. Ring handles 16 and 18 are shown in the closed position, i.e. when the two movable elements of working member 14 are closed together (as will be understood below). In this position there is a slight gap 22 between stop lugs 24 and 26. As will be understood below, gap 22 is provided in order to enable ring handles 16 and 18 to be squeezed together even after the movable elements (e.g. scissor blades) of working element 14 are "seated" in order to be sure that sufficient force is transmitted from actuating member 12 to working element 14.

The upper portion of ring handle 18 is fixedly connected to a hollow shaft 28 which serves to support other components of the instrument as will be understood below. An electrocautery post 30 may be provided in the event instrument 10 is to be used for electrosurgical procedures. The upper portion of ring handle 16 is provided with a receiving slot 32 adapted to accept the proximal, ball end of actuating rod 34. Pivoting motion of ring handles 16 and 18 translates to longitudinal reciprocating motion of actuating rod 34 relative to outer sleeve 28.

Referring now to FIGS. 2 and 3, working element 14 is shown in greater detail as comprising a pair of scissor blades 50 and 52 having proximal ends 54 and 56 and distal tips 58 and 60. The scissor blades are pivoted around pivot pin 62 which joins working element 14 to an adaptive coupling 64 secured to the distal tip of outer sleeve 28. Adaptive coupling 64 has a pair of opposing arms 66 and 68 within which working element 14 is mounted in a conventional manner. The distal tip of actuating rod 34 extends through an aperture in the base of adaptive coupling 64 and terminates in an apertured distal tip 70 which is joined to the proximal ends of intermediate connecting links 72 and 74 by a pivot pin 76. The distal ends of connecting links 72 and 74 are joined to the proximal ends 54 and 56 of the scissor blades, respectively, by pivot pins 78 and 80.

Figure 4B:
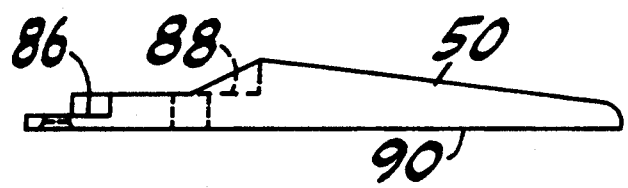
Figure 4C:
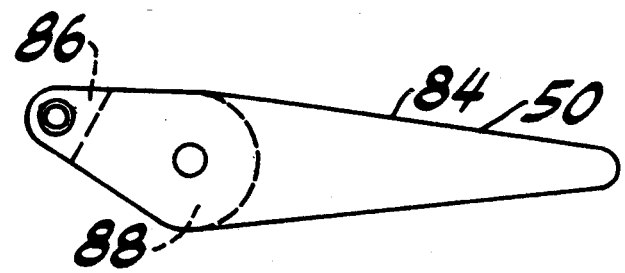
Figure 5A:
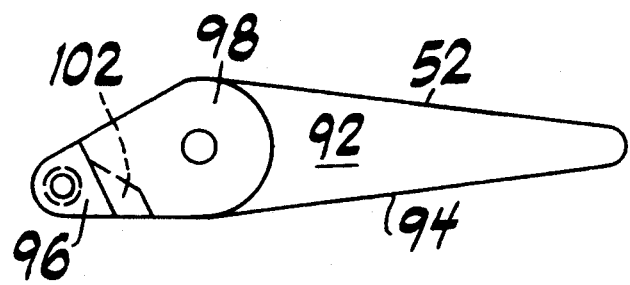
FIGS. 5a, b and c are top plan, side elevation and bottom views, respectively, of the other scissor blade of the instrument shown in FIG. 1.
Figure 5B:
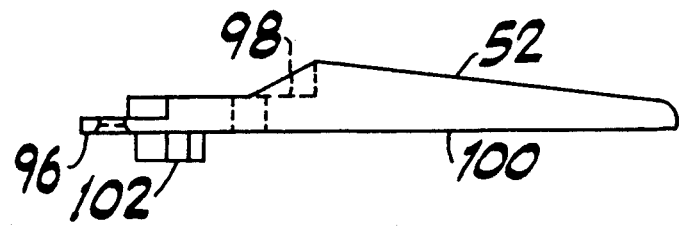
Figure 5C:
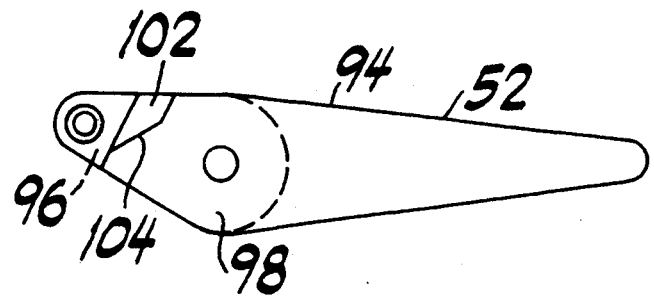

The structure of scissor blades 50 and 52 is best seen in FIGS. 4 and 5 wherein the a, b and c figures show the top plan, side elevation and bottom plan views of each scissor blade. Blade 50 has a tapered, semi-circular rounded body 82, a cutting edge 84, a link clearance cutout 86, a main pivot cutout 88 and a bottom surface 90. Similarly, blade 52 has a tapered, semi-circular body portion 92, a cutting edge 94, link clearance cutout 96, main pivot cutout 98 and lower flat surface 100. Scissor blade 52 is further provided with a stop member 102 having a stop surface 104 for abutting a portion of scissor blade 50 as will be better understood below.

Figure 6A:
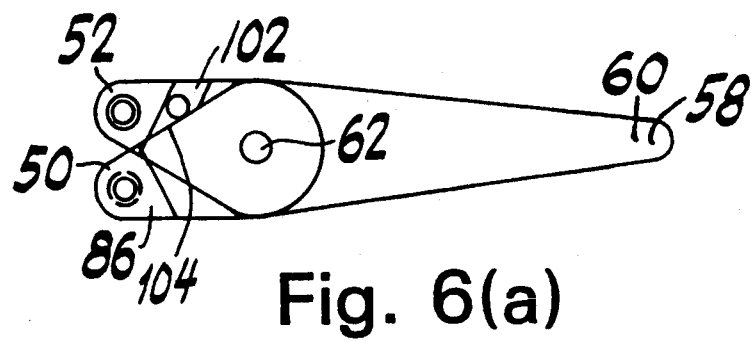
FIGS. 6a, b, c and d are diagrammatic assembly views of the scissor blades of FIGS. 4 and 5 joined together and shown in various stages of operation.
Figure 6B:
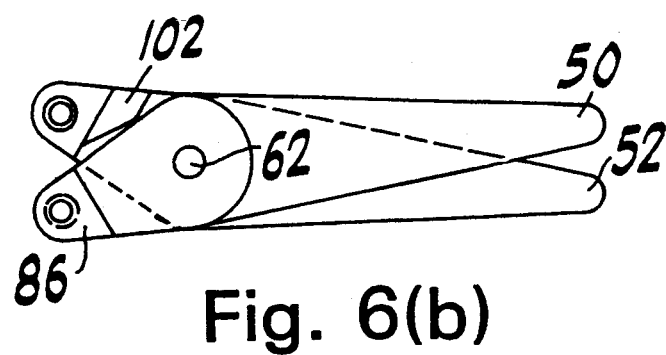
Figure 6C:
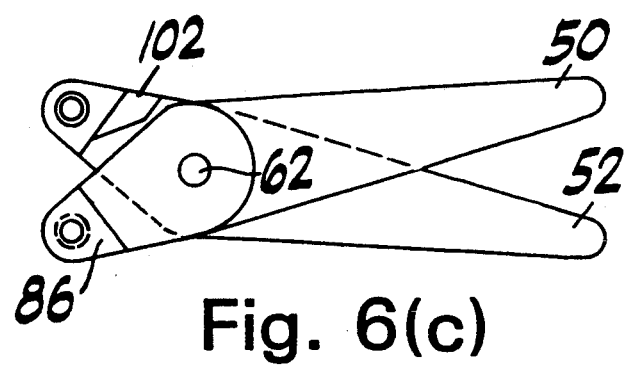
Figure 6D:
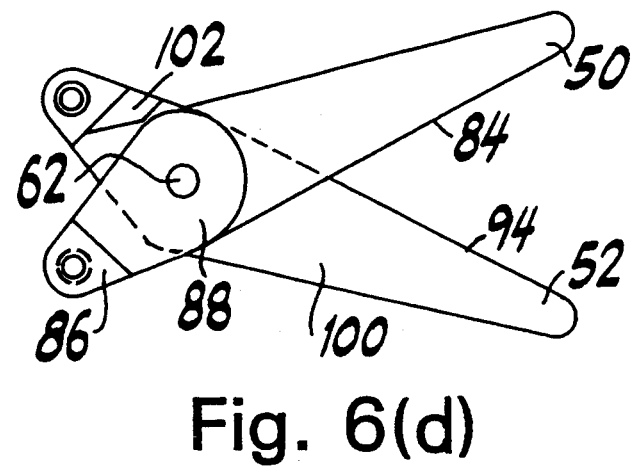

FIG. 6a shows scissor blades 50 and 52 in a fully closed position with stop surface 104 abutting the side of blade member 50 adjacent its proximal end 54. For clarity, links 72 and 74 and other associated components shown in FIGS. 2 and 3 are omitted from FIG. 6 although it should be understood that it is those components which produce the motion of the blades shown in FIG. 6 in response to the longitudinal motion of rod 34. FIGS. 6b, c and d show scissor blades 50 and 52 in various stages of opening.

When scissor blades 50 and 52 are in their fully closed position as shown in FIG. 6a, the distal tips 58 and 60 will be aligned. Stop member 102, by virtue of its positive limiting effect on the movement of blade 50 about pivot axis 62, assures that blade tips 58 and 60 will not travel past each other as the blades are closed. Because of the flat profile of surfaces 90 and 100, the distal tips 58 and 60 could easily pivot past each other if the ring handles 16 and 18 were not perfectly aligned in order to prevent this. Such would be the case in conventional endoscopic scissors wherein the cross-over of the tips is attempted to be prevented solely by keeping the handles from closing more than a certain amount. It will be understood that the invention, however, provides a way of positively limiting the over-travel of scissor blades in a secure and repeatable manner which is not dependent upon inconsistencies associated with the alignment of components at the proximal end of the instrument.

When ring handles 16 and 18 are situated as shown in FIG. 1, the scissor blades 50 and 52 will be urged into the closed position as shown in FIG. 6a. If tissue were interposed between the cutting edges 84 and 94 of the scissors, it may very well be that ring handles 16 and 18 would, because of the inherent elasticity of the components of the instrument, be almost totally squeezed together while the tissue prevents the scissor blades from closing. In such instances, additional force would need to be applied to ring handles 16 and 18 to complete the cutting action. If the scissors were of conventional design, the ring handles would be touching at this point and further squeezing would be impossible. The present invention, however, permits scissors 10 to be designed with a predetermined gap 22 between the ring handles since the positive stop between the scissor blades is provided by member 102 at the distal tip of the scissors. The gap permits greater squeezing force to be applied between the ring handles without causing crossover of the blade tips.

It will be understood by those skilled in the art that numerous modifications and improvements may be made to the preferred embodiment of the invention described herein without departing from the spirit and scope thereof.

What is claimed is:

1. Scissors for use in an endoscopic surgical procedure comprising:
    actuating means at the proximal end of the scissors to longitudinally reciprocate the elongated interconnecting means described below;

a pair of scissor blades at the distal end of the scissors, said scissor blades each having a proximal end and a distal end;

hinge means connected to the proximal ends of said scissor blades to pivot said scissor blades relative to each other in response to longitudinal motion of the elongated interconnecting means described below;

elongated interconnecting means for operatively joining said actuating means and said hinge means, said elongated interconnecting means having a proximal end and a distal end and adapted to be longitudinally reciprocated by said actuating means, said proximal end connected to said actuating means and said distal end connected to said hinge means; and stop means for preventing said distal ends of said scissor blades from crossing over each other, said stop means comprising an abutment affixed only to the proximal end of at least one of said scissor blades and engageable with the other of said scissor blades.

2. An instrument according to claim 1 wherein said stop means limits the travel of said scissor blades relative to each other as said actuating means are moved in one direction relative to each other and said stop means limits said scissor blades travel before said actuating means reach the limit of their range of motion.

* * * * *